United States Patent
Moumene et al.

(10) Patent No.: US 8,298,287 B2
(45) Date of Patent: Oct. 30, 2012

(54) INTERVERTEBRAL MOTION DISC WITH HELICAL SHOCK ABSORBER

(75) Inventors: Missoum Moumene, Newton, MA (US);
Richard Toselli, Barrington, RI (US);
Martin Masson, Keller, TX (US);
Payman Afshari, South Easton, MA (US)

(73) Assignee: DePuy Spine, Inc., Raynham, MA (US)

( * ) Notice: Subject to any disclaimer, the term of this patent is extended or adjusted under 35 U.S.C. 154(b) by 1330 days.

(21) Appl. No.: 11/768,615

(22) Filed: Jun. 26, 2007

(65) Prior Publication Data
US 2009/0005872 A1    Jan. 1, 2009

(51) Int. Cl.
*A61F 2/44* (2006.01)
(52) U.S. Cl. .................................... 623/17.16
(58) Field of Classification Search ..... 623/17.11–17.16
See application file for complete search history.

(56) References Cited

U.S. PATENT DOCUMENTS

| | | | |
|---|---|---|---|
| 2,730,159 A | 1/1956 | Germain | |
| 4,759,766 A | 7/1988 | Buettner-Janz | |
| 5,314,477 A | 5/1994 | Marnay | |
| 5,507,816 A | 4/1996 | Bullivant | |
| 5,676,701 A | 10/1997 | Yuan | |
| 5,824,094 A | 10/1998 | Serhan | |
| 5,827,328 A | 10/1998 | Buttermann | |
| 5,989,291 A | 11/1999 | Ralph | |
| 6,296,664 B1 * | 10/2001 | Middleton | 623/17.15 |
| 6,368,350 B1 | 4/2002 | Erickson | |
| 6,579,321 B1 * | 6/2003 | Gordon et al. | 623/17.16 |
| 6,582,468 B1 * | 6/2003 | Gauchet | 623/17.16 |
| 6,669,731 B2 | 12/2003 | Ralph | |
| 6,733,532 B1 * | 5/2004 | Gauchet et al. | 623/17.12 |
| 6,770,094 B2 * | 8/2004 | Fehling et al. | 623/17.13 |
| 6,964,686 B2 | 11/2005 | Gordon | |
| 6,969,405 B2 * | 11/2005 | Suddaby | 623/17.12 |
| 7,052,515 B2 * | 5/2006 | Simonson | 623/17.13 |
| 7,309,357 B2 * | 12/2007 | Kim | 623/17.13 |
| 7,331,994 B2 * | 2/2008 | Gordon et al. | 623/17.13 |
| 7,753,956 B2 * | 7/2010 | de Villiers et al. | 623/17.14 |
| 2002/0111681 A1 | 8/2002 | Ralph | |
| 2002/0111683 A1 | 8/2002 | Ralph | |
| 2002/0111685 A1 * | 8/2002 | Ralph et al. | 623/17.13 |
| 2003/0009223 A1 * | 1/2003 | Fehling et al. | 623/17.13 |
| 2003/0040802 A1 | 2/2003 | Errico | |
| 2003/0074073 A1 | 4/2003 | Errico et al. | |
| 2003/0220691 A1 | 11/2003 | Songer | |
| 2004/0024461 A1 * | 2/2004 | Ferree | 623/17.13 |
| 2004/0073310 A1 | 4/2004 | Moumene | |
| 2005/0027363 A1 * | 2/2005 | Gordon | 623/17.13 |
| 2005/0043804 A1 | 2/2005 | Gordon | |
| 2005/0065610 A1 | 3/2005 | Pisharodi | |
| 2005/0165486 A1 | 7/2005 | Trieu | |
| 2005/0228500 A1 | 10/2005 | Kim | |
| 2005/0234553 A1 | 10/2005 | Gordon | |
| 2005/0251260 A1 * | 11/2005 | Gerber et al. | 623/17.13 |
| 2006/0200239 A1 | 9/2006 | Rothman | |
| 2006/0200240 A1 | 9/2006 | Rothman | |

(Continued)

FOREIGN PATENT DOCUMENTS
WO    WO 2004016217    7/2004
(Continued)

*Primary Examiner* — Alvin Stewart
*Assistant Examiner* — Mary Hoffman

(57) ABSTRACT

This invention relates to an intervertebral motion disc having two opposing endplates, a central articulating core, and a peripheral helical shock absorber.

1 Claim, 5 Drawing Sheets

U.S. PATENT DOCUMENTS

| | | |
|---|---|---|
| 2006/0200241 A1 | 9/2006 | Rothman |
| 2006/0200242 A1 | 9/2006 | Rothman |
| 2006/0217809 A1 | 9/2006 | Albert |
| 2006/0293752 A1 | 12/2006 | Moumene |
| 2007/0168033 A1* | 7/2007 | Kim et al. .................. 623/17.13 |
| 2007/0299524 A1* | 12/2007 | Rivin .......................... 623/17.13 |
| 2008/0077246 A1* | 3/2008 | Fehling et al. ............. 623/17.16 |

FOREIGN PATENT DOCUMENTS

WO    WO 2005039455    5/2005

* cited by examiner

INTERVERTEBRAL MOTION DISC WITH HELICAL SHOCK ABSORBER

BACKGROUND OF THE INVENTION

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of articulation weight through a damaged, unstable vertebral joint. One proposed method of managing these problems is to remove the problematic disc and replace it with a prosthetic disc that allows for the natural motion between the adjacent vertebrae ("a motion disc").

U.S. Pat. No. 6,368,350 ("Erickson") discloses a three-piece motion disc providing two articulation surfaces. The disc comprises a first piece having a curved surface, a second piece having a flat surface, and an intermediate piece having a corresponding curved articulation surface and a corresponding flat articulation surface.

Erickson does not teach providing a shock-absorbing component in addition to the articulating component between the prosthetic endplates.

U.S. Pat. No. 5,676,701 ("Yuan") discloses, in one embodiment, a motion disc having a single articulation surface. This device includes a first component whose inner surface comprises a concave inner portion having a 360° circumference and a convex peripheral portion, and an opposing second component whose inner surface comprises a conforming convex inner portion and a convex peripheral portion. The convex/concave contours of the opposing inner portions forms a ball-and-socket design that allows unrestricted pivotal motion of the device, while the opposing convex peripheral contours allow flexion/extension bending motion in the range of about 20-30°.

However, Yuan does not teach providing a shock-absorbing component in addition to the articulating component between the prosthetic endplates.

U.S. Pat. No. 5,507,816 ("Bullivant") discloses a three-piece motion disc providing two articulation interfaces and comprises an upper piece having a flat lower surface, a middle spacer having a flat upper surface and a convex lower surface, and a lower piece having a concave upper surface. The articulating convex and concave surfaces form an articulating interface that allows pivotal motion, while the flat surfaces form a translation interface that allows translational motion.

Bullivant does not teach providing a shock-absorbing component in addition to the articulating component between the prosthetic endplates.

U.S. Pat. No. 4,759,766 ("Buttner-Janz") discloses a motion device comprising three components: an inferior endplate, a superior endplate, and a core having two articulation interfaces. Both the inferior and superior endplates are metal and have raised bosses with concave spherical surfaces in the center. The core is plastic and has convex surfaces on both the top and bottom which are surrounded by raised rims.

Buttner-Janz does not teach providing a shock-absorbing component in addition to the articulating component between the prosthetic endplates.

U.S. Pat. No. 5,314,477 ("Marnay") discloses a device having a single articulation interface and comprises three components: an inferior endplate, a superior endplate, and a plastic insert. The inferior endplate functions as a baseplate and has a sidewall forming an open ended channel for reception of the insert. The inner surface of the inferior endplate provides only stationary support for the insert and does not have a motion surface. Since the plastic insert is designed to be locked securely into place within the inferior endplate, the inferior surface of the insert is not a motion surface. The superior surface of the insert includes articulation surface for articulation with the superior endplate. The superior endplate has an inferior articulation surface that articulates with the superior motion surface of the plastic insert, and a superior surface designed for attachment to a vertebral endplate.

Marnay does not teach providing a shock-absorbing component in addition to the articulating component between the prosthetic endplates.

French Published Patent Application No. 2,730,159 ("Germain") discloses a motion disc in which the core member has one convex and concave surface. Germain further teaches that the radius of the upper curved surface ($3a$) of the core member is less than the radius of the lower curved surface ($3b$) of the core member.

Germain does not teach providing a shock-absorbing component in addition to the articulating component between the prosthetic endplates.

U.S. Pat. No. 5,824,094 ("Serhan") discloses a cushion-type motion disc wherein a rubber core is sandwiched between two metal prosthetic endplates. The rubber core provides a shock-absorbing effect and so mimics the natural response to axial load. However, the rubber core was found to experience high shear stresses in use.

U.S. Pat. No. 6,579,321 ("Gordon I") discloses an implantable disc that comprises a support ball that acts as a pivot point. The support ball is of the constrained type and does not represent a mobile, free-floating type of core since the core is fixed and the motion of the disc occurs about a fixed center (the center of the ball). Additionally, the support ball has only a single contact surface.

U.S. Pat. No. 6,964,686, US Published Patent Applications US20050027363, US20050043804, US20050234553, and WO2005039455 ("Gordon II") discloses a disc that comprises a first piece having a curved surface, a second piece having a flat surface, an intermediate piece having a corresponding curved articulation surface and a corresponding flat articulation surface, and a helical spring encasing the device. However, Gordon does not teach providing an intermediate piece (the core) having opposed convex surfaces. By not doing so, Gordon fails to recognize the advantages provided by a "floating" mobile core. It is believed that a free motion or "floating" core provides a better way to duplicate the instantaneous articulating center of rotation of the natural disc.

U.S. Pat. Nos. 5,989,291 and 6,669,731 and US Published Patent Applications US20020111681, US20020111683, US20030040802, and US20030074073 ("Ralph") disclose certain devices that provide rotational motion to the functional spinal unit by means of a spherical ball articulating in a corresponding socket, while translational motion about the vertical axis is allowed to a certain degree via at least one Belleville washer or similar feature. Ralph did not consider utilizing a mobile core and instead used a fixed core.

PCT Patent Publication No. WO2004016217 ("Gerber") discloses a multi-piece device having one or more helical springs with one or both ends articulating via a curved surface. This type of device does not present a combination of a free floating, mobile, convex-convex core and a helical shock absorber.

US Published Patent Application No. 20040073310 ("Moumene") discloses an intervertebral disc having two opposite endplates, a central articulating core, and a peripheral shock absorber. The peripheral shock absorber is not in the form of a helix.

US Published Patent Application No. 20050065610 ("Pisharodi") discloses a rotating, spring-loaded implant that only provides for pre-loading elements forming the arthroplasty device.

US Published Patent Application No. 20050228500 ("Kim") discloses upper and lower endplates separated by a compressive core member, wherein the device stiffness is controlled independently by adjusting the components of the disc. A helical shock absorber is disclosed as being located inside the articulating core.

US Published Patent Application No 20050165486 ("Trieu") discloses a device that resists at least one predetermined directional motion between first and second components. However, Trieu does not teach providing a helical shock absorber in addition to the articulating component between the prosthetic endplates.

US Published Patent Application No. 2006/0200242 ("Rothman I") discloses an intervertebral stabilizer including a first surface operable to engage an endplate of a first vertebral bone of a spine; a second surface spaced apart from the first surface and operable to engage an endplate of an adjacent second vertebral bone of the spine; and a spring element between the first and second surfaces and operable to provide a reactive force in response to compression loads from the first and second vertebral bones, wherein a cross-sectional profile taken through the spring is hourglass shaped.

US Published Patent Application No. 2006/0217809 ("Albert I") discloses an intervertebral stabilizer including a first plate member operable to engage an endplate of a first vertebral bone of a spine; a second plate member spaced apart from the first plate member and operable to engage an endplate of an adjacent second vertebral bone of the spine; a ball element depending from the first plate member; and a socket element depending from the second plate member, wherein at least one of the ball and socket elements include one or more keyed surfaces such that (i) an assembly function is obtained in which the ball element may at least one of be received into, and removed from, the socket element in one or more first articulation positions of the first and second plate members; and (ii) a capture function is obtained in which the ball element may at least one of not be received into, and not be removed from, the socket element in one or more second articulation positions of the first and second plate members.

US Published Patent Application No. 2006/0200241 ("Rothman II") discloses an intervertebral stabilizer including a first surface operable to engage an endplate of a first vertebral bone of a spine, a second surface spaced apart from the first surface and operable to engage an endplate of an adjacent second vertebral bone of the spine; a spring element between the first and second surfaces and operable to provide a reactive force in response to compression loads from the first and second vertebral bones, wherein a cross-sectional profile taken through the surfaces is hourglass shaped.

US Published Patent Application No. 2006/0200240 ("Rothman III") discloses a lumbar intervertebral stabilizer for a lumbar region of a spine, including a first surface operable to engage an endplate of a first vertebral bone of a spine; a second surface spaced apart from the first surface and operable to engage an endplate of an adjacent second vertebral bone of the spine; a spring element including at least one of (i) a helical wound spring; and (ii) a hollow body having at least one slit forming a plurality of annular circumferential helical coils, the spring element being disposed between the first and second surfaces and being operable to provide a reactive force in response to compression loads from the first and second vertebral bones, wherein at least some diameters of the respective turns of the helical coils differ.

US Published Patent Application No. 2006/0200239 ("Rothman IV") discloses a posterior intervertebral stabilizer including a first stabilizing element having (i) a first surface operable to engage an endplate of a first vertebral bone of a spine, and (ii) a second surface spaced apart from the first surface and operable to engage an endplate of an adjacent second vertebral bone of the spine; a second stabilizing element having (i) a first surface operable to engage an endplate of the first vertebral bone of the spine, and (ii) a second surface spaced apart from the first surface and operable to engage an endplate of the adjacent second vertebral bone of the spine, each including helical coils disposed between the respective first and second surfaces of the first and second stabilizing elements, each operable to provide a reactive force in response to compression loads from the first and second vertebral bones, wherein at least some diameters of respective turns of the respective helical coils differ.

US Published Patent Application No. 2003/0220691 ("Songer") discloses a motion disc having an upper endplate, a lower endplate, an articulating core therebetween and a peripheral shock absorber disposed around the core. See FIG. 11G.

SUMMARY OF THE INVENTION

The present invention relates to an intervertebral motion disc comprising opposing endplates, an intermediate portion comprising a central articulating core component and a peripheral helical shock-absorbing component. In particular, the invention is an artificial disc with a mobile core peripherally constrained by a helical shock absorber.

In preferred embodiments, the central articulating core component is adapted to articulate with each of the opposing endplates and thereby maintain the proper intervertebral spacing and full range of motion. The surrounding shock-absorbing component provides the stiffness and shock-absorbing qualities of the natural disc in both flexion and torsion while centrally maintaining the core. The helical nature of the shock absorber advantageously provides controlled range of motion in axial rotation (torsional stiffness).

The core, generally cylindrical or elliptical in shape, preferably has upper and lower convex surfaces that articulate above with an upper endplate and below with a lower endplate. Both endplates preferably have corresponding concave inner articulation surfaces. In one preferred embodiment, the endplates are threaded about their peripheral rims and can be screwed onto the ends of the shock absorber.

Therefore, in accordance with the present invention, there is provided a motion disc comprising:

a) a first prosthetic vertebral endplate comprising:
  i) an first outer surface adapted to mate with a first vertebral body,
  ii) an first inner surface comprising an first peripheral surface and a first articulation surface, and
  iii) a body portion connecting the first inner and outer surfaces, b) a second prosthetic vertebral endplate comprising:
  i) an second outer surface adapted to mate with a second vertebral body,
  ii) an second inner surface comprising a second peripheral surface and a second articulation surface, and
  iii) a body portion connecting the second inner and outer surfaces, c) an articulating core member comprising:
   i) a first articulation surface adapted for articulation with the first articulation surface of the first endplate, and
   ii) a second articulation surface adapted for articulation with the first articulation surface of the second endplate, and
d) a peripheral, helical shock-absorbing component comprising:
   i) a first end portion contacting the first endplate,
   ii) a second end portion contacting the second endplate, and
   iii) an axial channel,
wherein the core member is disposed within the axial channel of the helical shock-absorbing component and oriented therein to produce a first articulation interface between the first articulation surface of the first endplate and the first articulation surface of the core member, and a second articulation interface between the first articulation surface of the second endplate and the second articulation surface of the core member.

DETAILED DESCRIPTION OF THE INVENTION

For the purposes of the present invention, "prosthetic vertebral endplate" broadly describes a component designed to substantially fit within an intervertebral space and mate with an opposing surface of one of the adjacent vertebral bodies. The "prosthetic vertebral endplate" includes all geometric configurations, including but not limited to substantially thin and substantially blocky configurations. Types of mating include, but are not limited to, penetrating the adjacent vertebral body, simply contacting the adjacent vertebral body, and providing fixation through a third component such as a fastener (such as a screw) that is received within or connected to the prosthetic vertebral endplate. Such fixation may occur upon a non-opposing surface of the adjacent vertebral body (such as the anterior wall of the vertebral body). The adjacent vertebral body may be prepared or unprepared so that the contacting surface thereof may include the cortical endplate portion of the vertebral body or the internal cancellous portion of the vertebral body.

For the purposes of the present invention, a "substantially curved articulation interface" produces substantially pivotal motion during articulation. Examples of such substantially curved interfaces include but are not limited to hemispherical interfaces having a radius of between about 10 mm and about 30 mm.

For the purposes of the present invention, both "slightly curved articulation interfaces" and "substantially flat articulation interfaces" produce substantially translational motion during articulation. Examples of such "slightly curved interfaces" include but are not limited to hemispherical interfaces having a radius of between about 40 mm and about 100 mm. For the purposes of the present invention, a "substantially flat articulation interface" is sufficiently flat so as to allow axial rotation of either mating component at any point along the interface.

Figure 1:
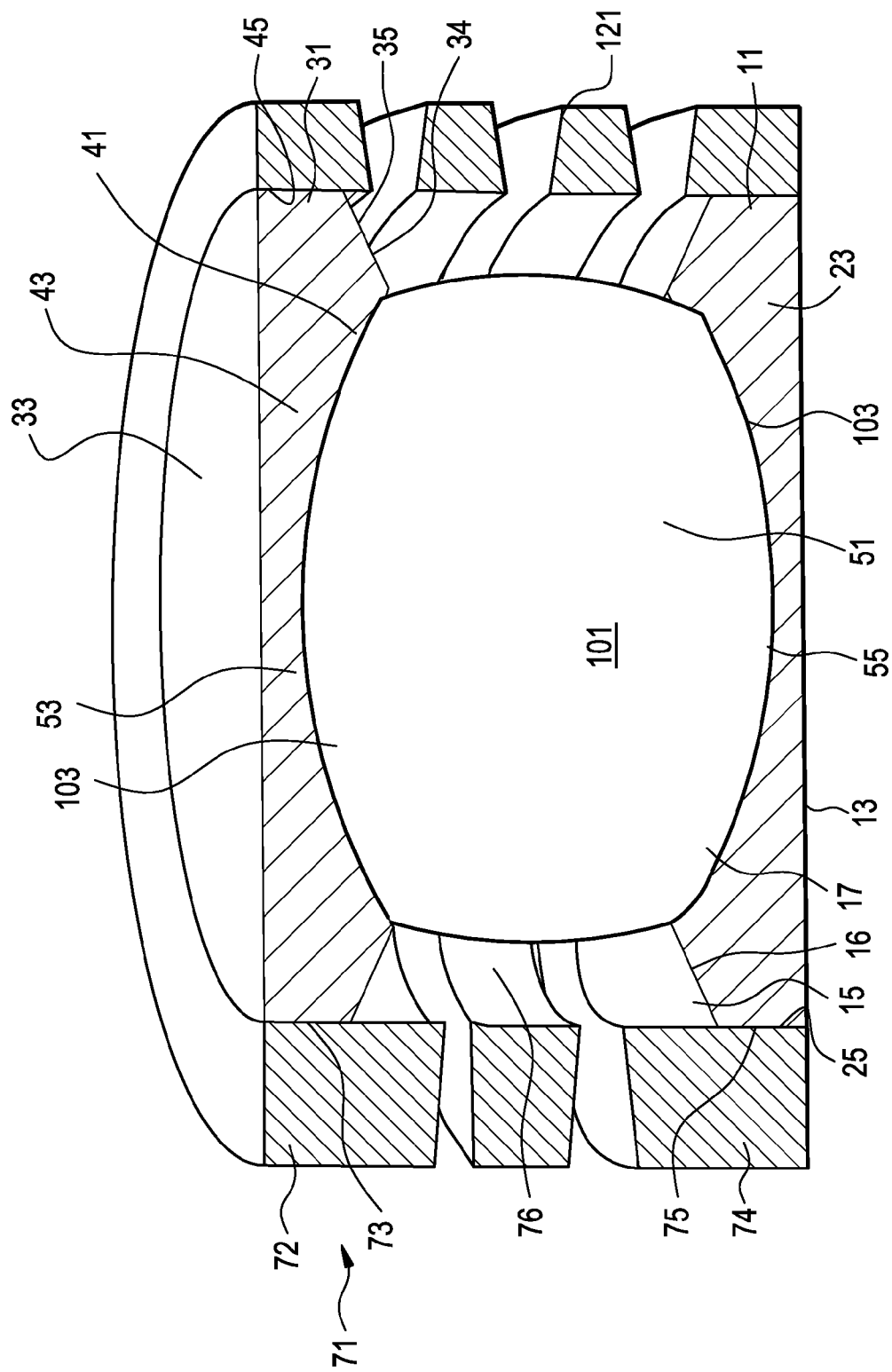
FIG. 1 discloses a cross-sectional view of an embodiment of the motion disc of the present invention.

Now referring to FIG. 1, there is provided a motion disc 1 comprising:
a) a first prosthetic vertebral endplate 31 comprising:
   i) an outer surface 33 adapted to mate with a first vertebral body,
   ii) an inner surface 35 having an peripheral surface 34 thereon and a first articulation surface 41,
   iii) a body portion 43 connecting the inner and outer surfaces and defining a sidewall 45,
b) a second prosthetic vertebral endplate 11 comprising:
   i) an outer surface 13 adapted to mate with a second vertebral body, and
   ii) an inner surface 15 comprising a peripheral surface 16 and a first articulation surface 17,
   iii) a body portion 23 connecting the inner and outer surfaces and defining a sidewall 25,
c) an articulating core member 51 comprising:
   i) a first articulation surface 53 adapted for articulation with the first articulation surface of the first endplate, and
   ii) a second articulation surface 55 adapted for articulation with the first articulation surface of the second endplate,
d) a peripheral, helical shock-absorbing component 71 comprising:
   i) an upper end portion 72 having an inner rim 73 contacting the sidewall of the first endplate, and
   ii) a lower end portion 74 having an inner rim 75 contacting the sidewall of the second endplate, and
   iii) an axial channel 76,
wherein the core member is disposed within the axial channel of the helical shock-absorbing component and oriented therein to produce a first articulation interface between the first articulation surface of the first endplate and the first articulation surface of the core member, and a second articulation interface between the first articulation surface of the second endplate and the second articulation surface of the core member.

Figure 2:
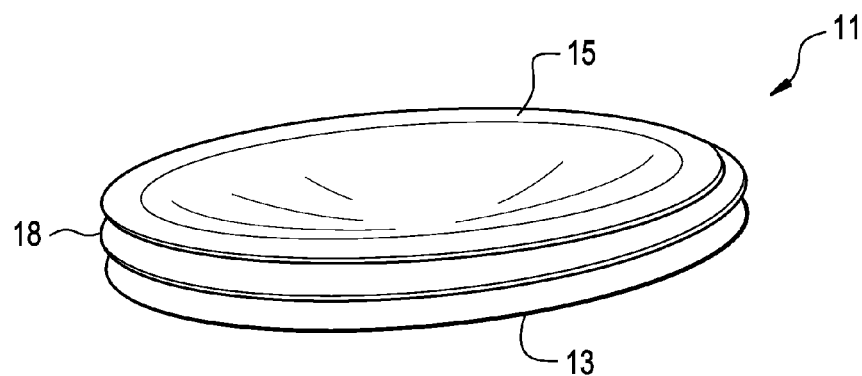
FIG. 2 discloses an endplate of the present invention.

Generally, the device comprises four main components: an inferior endplate 11, a superior endplate 31, a centrally disposed articulating core member 51, and a peripheral helical shock absorber 71. Each of the four main components of one preferred embodiment will now be described in more detail:

Now referring to FIG. 2, both endplates have corresponding substantially curved concave articulation surfaces. In one preferred embodiment, the peripheral rim 18 of the endplate is threaded and can be screwed onto the shock absorber.

Now referring to FIGS. 1 and 2, in one embodiment, inferior endplate 11 has an inferior surface 13 designed to mate with a natural vertebral endplate, a superior surface 15 whose central portion is designed for articulation with the core member, a body portion 23 therebetween, and a peripheral sidewall (or rim) designed for attachment (preferably, tenacious or threaded attachment) to the shock-absorbing member.

Preferably, the inferior (outer) surface 13 of this endplate is either flat, curved or domed to match the shape of the natural vertebral endplate. Alternatively, the geometry of the inferior surface can be designed so that it will match the shape of the patient's vertebral endplate after the vertebral endplate has been modified by an endplate-shaping instrument. In addition, the inferior surface of this prosthetic endplate can further comprise features adapted to promote and secure initial fixation and bony ingrowth including, but not limited to, spikes, keels, teeth, projections (such as dovetails), recesses (such as grooves) and porous coatings.

Superior (inner) surface 15 comprises a non-articulating peripheral portion 16 and a a highly polished substantially concave articulation surface 17 designed to mate with a corresponding substantially convex articulation surface disposed upon the core member. Preferably, substantially concave articulation surface 17 is further designed to conform to the corresponding concave articulation surface of the core. In the preferred embodiment, the articulation surface 17 is concave. However, the substantially curved articulation surface can also be convex if desired to mate with a corresponding substantially concave articulation surface (not shown) disposed upon the core member. Preferably, the substantially curved articulation surface 17 has been polished to a surface roughness Ra of no more than 100 nm.

Figure 5A:
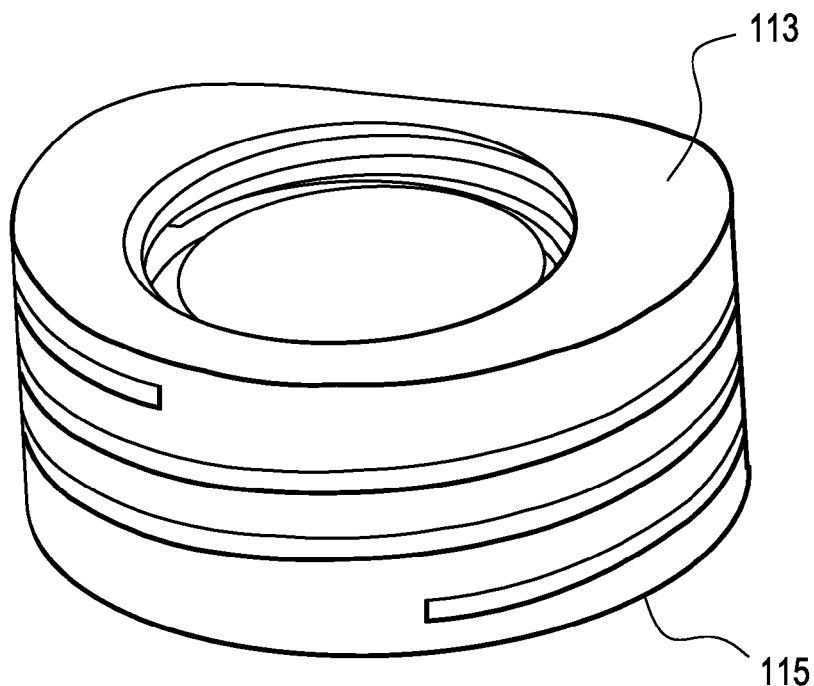
FIG. 5a discloses a core contained within the helical shock absorber of the present invention.
Figure 5B:
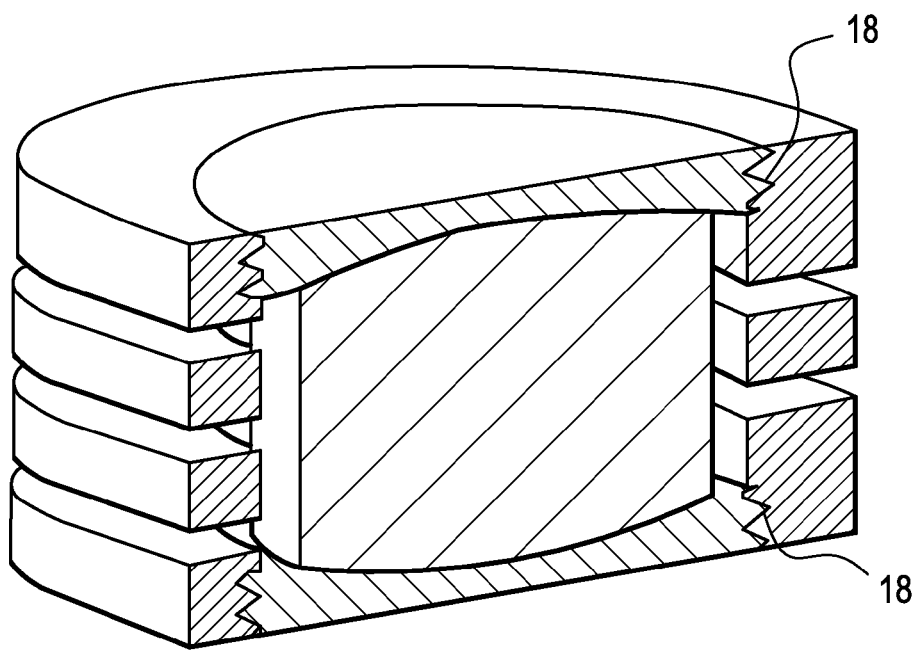
FIG. 5b discloses a threaded connection between the endplates and shock absorber of the present invention.

In some embodiments, and now referring to FIGS. 2 and 5b, this endplate has a peripheral outer sidewall 18 (or rim 18) that is threaded. This thread is designed to mate with a corresponding thread upon the inner surface of the helical shock absorber and allow easy coupling of these components.

Now referring to FIGS. 1 and 2, superior endplate 31 has a superior outer surface 33 designed to mate with the vertebral endplate, an inferior inner surface 35 whose central portion is designed for articulation with the core member, a body portion 43 therebetween, and a peripheral rim designed for attachment (preferably, tenacious or threaded attachment) to the shock-absorbing member.

Preferably, the superior outer surface 33 of this endplate is either flat, curved or domed to match the natural vertebral endplate. Alternatively, the geometry of the superior surface can be designed so that it will match the shape of the patient's vertebral endplate after the vertebral endplate has been modified by an endplate-shaping instrument. In addition, the superior surface of this prosthetic endplate can further comprise features adapted to promote secure initial fixation and bony ingrowth including, but not limited to, spikes, keels, teeth, projections (such as dovetails), recesses (such as grooves) and porous coatings.

Inferior (inner) surface 35 comprises a non-articulating peripheral portion 34 and a a highly polished substantially concave articulation surface 41 designed to mate with a corresponding substantially convex articulation surface disposed upon the core member. Preferably, substantially concave articulation surface 41 is further designed to conform to the corresponding convex articulation surface of the core. In the preferred embodiment the articulation surface 41 is concave. However, the substantially curved articulation surface can also be convex if desired to mate with a corresponding substantially concave articulation surface (not shown) disposed upon the core member. Preferably, the substantially curved articulation surface 41 has been polished to a surface roughness Ra of no more than 100 nm.

In some embodiments, and now referring to FIGS. 2 and 5b, the superior endplate has a peripheral outer sidewall 18 (or rim 18) that is threaded. This thread is designed to mate with a corresponding thread upon the inner surface of the helical shock absorber and allow easy coupling of these components.

In some devices, the body portion of each endplate is thicker in the anterior portion than in the posterior portion. This difference provides the implant with desirable lordosis. Preferably, the angle of lordosis provided by the implant is between 5 and 20 degrees. More preferably, the angle of lordosis provided by the implant matches that of an intact healthy disc for the given level of implantation. In other embodiments, the thickness of the body portion of each endplate is equal in its posterior and anterior portions.

In yet another preferred embodiment, at least one endplate is bipartite or multipartite to provide a means to alter the height of the device. In this embodiment, the surgeon has the option to increase or reduce the height of the device to make it better conform to the intervertebral space. In one embodiment thereof, the means to alter the height of the device comprises a threaded element that screws onto an endsurface of the endplate directly facing the vertebral body. Accordingly, varying the number of turns (and thereby the extent of inter-engagement of the components) becomes a way to alter the device's overall height.

The outer surfaces of the endplates are designed to directly oppose the patient's vertebral bodies, and can be either flat, concave, or convex, and can be macro- or micro-textured. Texturing may be used to provide a means to attach the device to the vertebral bodies or to enhance another existing means of attaching the endplates to the biological structure. The attachment can be mechanical, biologic (to provide bone ingrowth) or both.

In a preferred embodiment, the outer surfaces of the endplates are hydroxyapatite-coated to provide a means to enhance bone ingrowth therein. In another embodiment, the endplates are cemented to the vertebral bodies. In another proposed embodiment, the endplates have keels that match surfaces in the vertebral bodies that have been prepared by the surgeon. In another proposed embodiment, the endplates have metallic protrusions (such as spikes) that hold the device in place when force-pressed into bone.

(Core)

In a preferred embodiment, the articulating core member consists essentially of a cylinder having two convex ends adapted for articulation.

Figure 3:
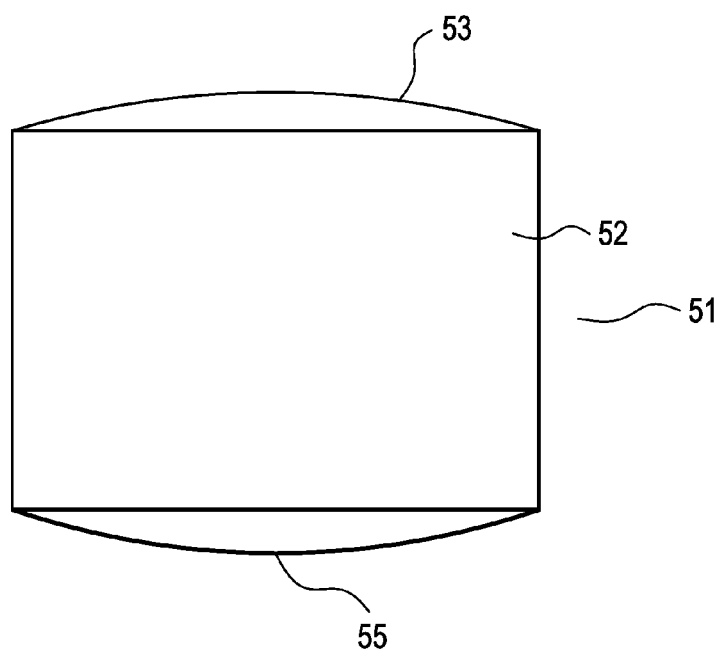
FIG. 3 discloses a core of the present invention.

Now referring to FIGS. 1 and 3, the core member 51 comprises a body portion 52 forming a convex superior surface 53 that is designed to articulate with the bottom surface 41 of the superior endplate and a convex inferior surface 55 that is designed to articulate with the upper surface of the inferior endplate. In some preferred embodiments, the body portion has a substantially cylindrical body portion 52. Preferably, superior surface 53 is further designed to conform to the bottom surface 41 of the superior endplate. Also preferably, convex inferior surface 55 is designed to conform with a corresponding substantially curved upper surface of the inferior endplate. In some embodiments (not shown), one of the core articulation surfaces is substantially flat to provide substantially translational motion with a corresponding flat bottom surface of a corresponding endplate. However, in other embodiments, one of the core articulating surfaces is slightly curved to provide substantially translational motion with a correspondingly curved surface of the corresponding endplate as well as soft resistance to extreme translational motion.

The substantially curved articulation surfaces of the core can be any shape designed for pivotal articulation, including hemispherical, hemicylindrical, hemi-ellipsoidal, and oblong. However, in preferred embodiments, the curved surface has a spherical portion. In the preferred embodiments, the substantially curved articulation surfaces of the core are convex. However, the curved articulation surface can also be concave, if desired, to mate with a corresponding substantially convex articulation surface disposed upon an endplate.

The substantially curved articulation surfaces of the core may be modified to any slightly curved geometry that allows at least one degree of substantially translational motion, including a hemi-cylindrical shape.

Preferably, the radius of each of the upper and lower articulation surfaces of the core is between about 40 mm and about 100 mm. Below 40 mm, the depth of the curve requires adding significantly more material to the corresponding endplate, thereby increasing the height of the implant. Above 80 mm, the curve provides a less significant braking.

Preferably, the non-spherical curved articulation surfaces of the core are hemicylindrical surfaces, as such a surface can articulate with a similar opposing hemicylindrical surface and in some embodiments provide conforming articulation therewith. Also preferably, the curved dimension of the hemicylindrical surface is provided in the A-P direction (to provide a soft braking) while the linear dimension is provided in the medial-lateral direction. However, in other embodiments, the curved dimension of the hemicylindrical surface is provided in the medial-lateral direction, while the linear dimension is provided in the anterior-posterior direction.

In other embodiments, the hemispherical surface is substantially curved and the curved, non-hemispherical surface with which it articulates is slightly curved. In other embodiments, the hemispherical surface is substantially curved and the curved, non-hemispherical surface with which it articulates is slightly curved. In one preferred embodiment, the mobile core has two opposing convex surfaces separated by a body portion that is cylindrical in shape.

Alternatively, the body portion of the core has an axially changing curvature that is either turned inwardly or outwardly. An inward curvature provides a core having a dumbbell shape. An outward curvature confers to the core the shape of a bulging cylinder. In yet another embodiment, the mobile core has essentially no cylindrical body portion, i.e., the two convex surfaces converge to form a line, producing a flying saucer shape.

In yet another embodiment, the core has two convex faces and an axial through hole that gives it the shape of a toroid. In yet another embodiment, the core has at least one blind hole in it. In yet another embodiment, the core has an upper blind hole and a lower blind hole.

The core can be adapted to be removable and replaceable in situ. Since the core is not attached to any single part, it can be removed from the device and replaced in the operating room by the surgeon by conveniently unscrewing one of the endplates.

In some embodiments, the core is rigid. Alternatively, the core can have a resilient portion. Such a resilient core can be made with the same materials used in an artificial disc nucleus. A resilient core will add flexibility in compression-distraction and may advantageously affect the motion disc's response to other loading modes as well.

The core can be made bipartite or multipartite. The core may possess a single stiffness or several stiffnesses depending on the type of material employed and the number of different materials employed.

In one embodiment, the material selected for the core allows it to act as an additional shock absorber. In another embodiment, and now referring to FIG. 1, the inner portion 101 of the core is resilient while the convex ends 103 of the core have hard articulation surfaces that allow their quasi-frictionless sliding with the prosthetic endplates.

In yet another embodiment, the core is made out of polyethylene and is inserted into a cylindrical (preferably metallic) tube that leaves both convex ends free to contact the prosthetic endplates while the side walls are protected from wear abrasion that may arise from contacting the shock absorber inner rim. Alternatively, the protecting tube can be shaped as a dumbbell or a bulging cylinder.

In yet another embodiment, the core and/or the endplates have articulation surfaces that are hardened using material deposition processes such as diamond-like coating.

Figure 4A:
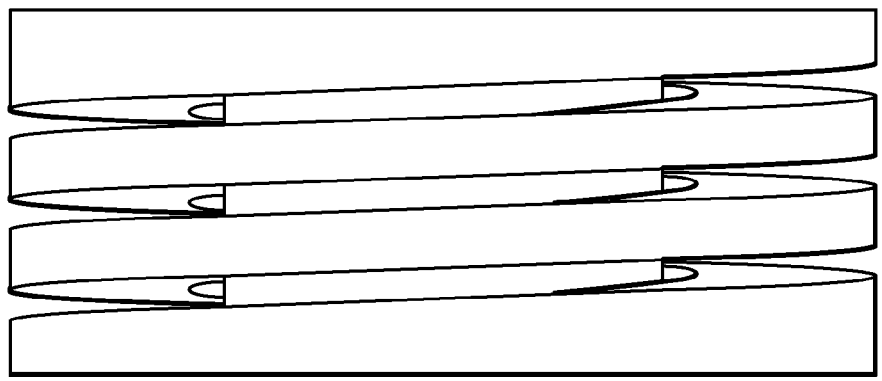
FIGS. 4a and 4b disclose side and cross-sectional views of a helical shock absorber of the present invention.

The shock absorber is a helical shock absorber with predetermined properties. Now referring to FIGS. 1, 4a and 4b, the shock absorber is essentially a helical shock absorber that provides flexural and torsional resistance.

The primary function of the shock-absorbing component is to provide axial and torsional stiffness and dampening. In some embodiments, the material of the shock-absorbing component is selected to provide a spring constant of between about 500 N/mm and 1000 N/mm. When the shock-absorbing component is so designed, it can absorb between about 5,000N and 10,000 N of axial load.

Figure 4B:
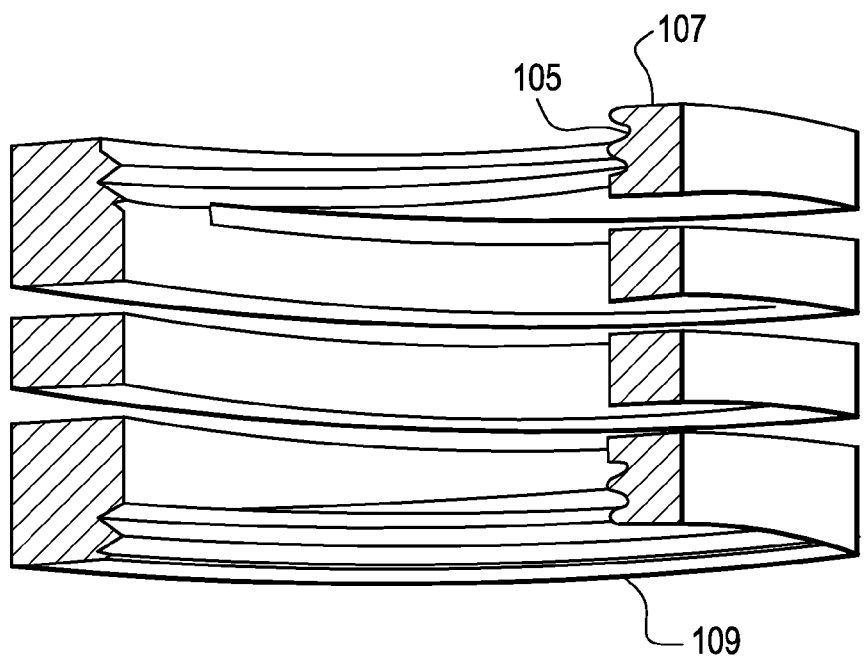

In a preferred embodiment (as shown in FIGS. 4b and 5b), the shock absorber has a threaded inner rim 105 at the upper 107 and lower 109 ends thereof, and each prosthetic endplate has a mating threaded outer rim (18 in FIG. 2) that allows each endplate to be threaded into a respective end of the shock absorber.

In another embodiment (as shown in FIG. 1), the shock-absorbing component is tenaciously attached to the peripheral sidewall (or rim) of the opposing endplates. The methods disclosed in Serhan, supra, are suitable for providing such attachment. The tenacious attachment mitigates wear concerns at this interface. When the peripheral shock-absorber is tenaciously attached, the issue of assembling the core into the central space must be addressed. In some embodiments (not shown), at least one of the endplate endsurfaces is modified with a central window whose edge is threaded for threaded reception of a threaded plug. In this case, the peripheral shock-absorber can be tenaciously attached to the endplates with the window open, the core can be inserted through the open window, and then the window can be closed with the threaded plug.

Now referring to FIG. 5b, the upper 113 and lower 115 surfaces of the helical shock absorber can also be adapted to threadably attach to vertebral endplates in the manner described above for the endplate components.

Among the variables that can modulate the shock absorber characteristics are: material, height, outside diameter, inside diameter, number of coils, pitch, coil diameter, coil shape, helix shape, and the number of helices (e.g., one, two, three, or more). These variables can be modulated to provide a shock absorber that operates over a linear range or, alternatively, over a non-linear range.

In one embodiment, the shock absorber is made from a single piece (i.e., is integral). In another embodiment, the shock absorber is bipartite or multipartite. In yet another embodiment, the shock absorber comprises a wear-resistant sheath or bellows (not shown) that cushions the helical inner rim. The sheath shields the core from directly contacting the coil and thereby prolongs the life of the device by enhancing its wear resistance.

Now referring to FIG. 1, in some embodiments, the coils of the shock absorber are chamfered 121 to form a trapezoidal cross-section. These chamfers provide an enhanced range of motion to the shock absorber. Therefore, in some embodiments, there is provided an intervertebral motion disc comprising:

a) a first prosthetic vertebral endplate comprising:
      i) a first outer surface adapted to mate with a first vertebral body,
      ii) a first inner surface comprising an first peripheral surface and a first articulation surface,
      iii) a body portion connecting the first inner and outer surfaces, b) a second prosthetic vertebral endplate comprising:
  i) a second outer surface adapted to mate with a second vertebral body, and
  ii) a second inner surface comprising a second peripheral surface and a second articulation surface,
  iii) a body portion connecting the second inner and outer surfaces,
c) a peripheral, helical shock-absorbing component comprising:
  i) a first end portion contacting the first endplate, and
  ii) a second end portion contacting the second endplate, and
  iii) a coil forming an axial channel, wherein a transverse cross section of the coil is chamfered,
wherein the first articulation surface opposes the second articulation surface, and wherein the first and second endplates are present within the axial channel of the shock-absorbing component.

Now referring to FIG. 5a, the mobile (or "floating") core lies inside the axial channel of the helical shock absorber. Hence, a means for preventing the core from being expulsed from the intervertebral space is provided by the shock absorber. When the helical shock absorber is affixed to both endplates and substantially encases the free floating core, and when both endplates are rigidly joined to the upper and lower vertebral bodies, it is not possible for the core to migrate outside of the intervertebral space. Thus, this arrangement provides enhanced safety.

In preferred embodiments, a gap exists between the core and the inside rim of the helical shock absorber. This gap allows the core to freely float (i.e., move side to side) to a certain degree. Since the core remains encased inside the shock absorber, the extent of motion of the core is limited by the lateral resistance provided by contact with the inner rim of the helical shock absorber.

The prosthetic endplates may be attached to the shock absorber by any number of means. In one embodiment, the endplates are screwed onto the shock absorber. In another embodiment, the junction of the two parts is seamless—either the two parts are welded or the endplate/shock absorber is machined as one single piece so that at least one endplate is integral to the shock absorber. In yet another embodiment, at least one endplate is joined to the shock absorber by an interference fit. In yet another embodiment, at least one endplate is joined to the shock absorber with a taper lock.

Finite Element Analysis (FEA) was used to predict the response of the device of the present invention to physiologic loading. Now referring to FIG. 1, in one particular FEA test, the overall height of the device was set at about 10 mm while the cross-sectional length was set at about 24 mm. The device of FIG. 1 was characterized by a maximal flexion of 10 degrees [Fl(10°)], a maximum extension of 10 degrees [Ext(10°)], a maximum axial rotation of +/−3 degrees [AR(+/−3°)], and a maximum lateral bending of +/−5 degrees [LB(+/−5°)]. In the test, the upper left hand corner of the device was subjected to a purely axial load of 74N such that the upper left hand corner was displaced by about 2 mm.

Figure 6A:
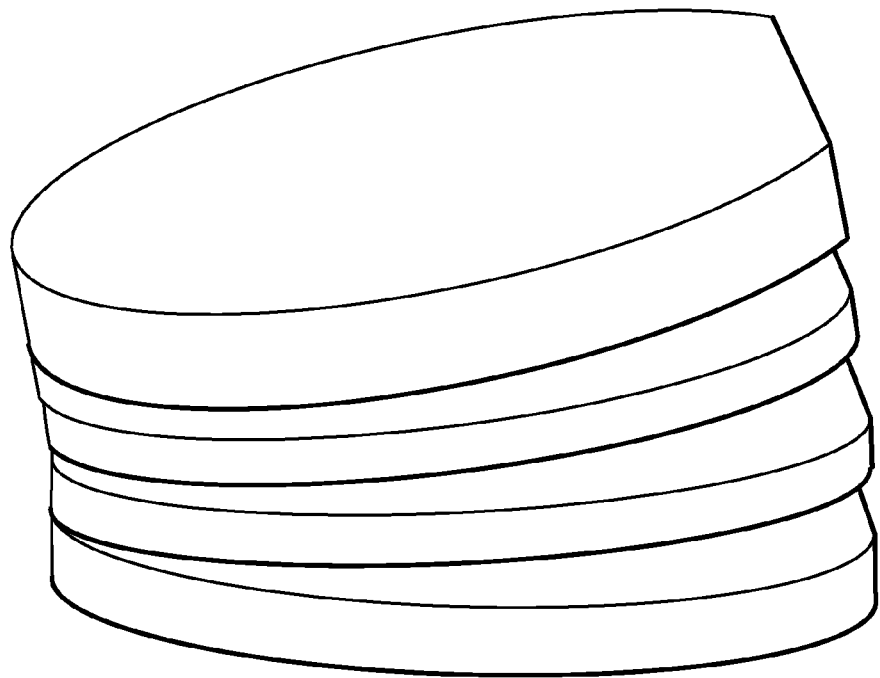
FIG. 6a discloses a perspective view of the response of the device of FIG. 1 to physiologic flexion.
Figure 6B:
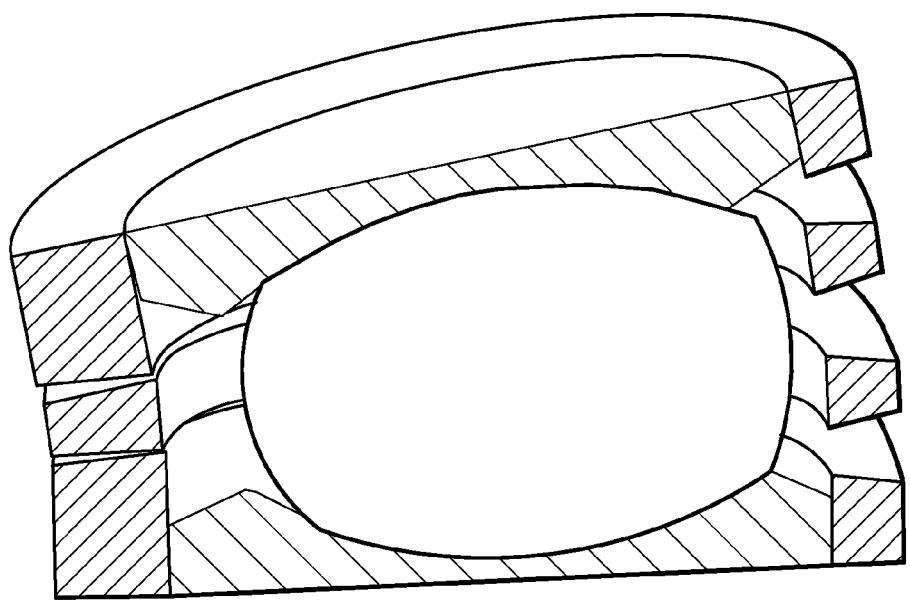
FIG. 6b discloses a cross-sectional view of the response of the device of FIG. 1 to physiologic flexion.

Now referring to FIGS. 6a-6b, there are provided the responses of the motion disc of the present invention to an anteriorly-located axial load. FIGS. 6a and 6b disclose the displacement responses of the device. Review of these figures indicates that the greatest displacement occurs in the areas closer to the upper left hand corner of the device. Further review also reveals that the left hand portion of the shock-absorbing component is essentially reduced in height (to about 8 mm), while the right hand portion of the shock-absorbing component is essentially increased in height (to about 11 mm).

Also as shown in FIG. 6b, the core component of the device responds to this anterior load by shifting posteriorly. This movement shifts the center of rotation of the motion device. Since it is known that the center of rotation of the natural intervertebral disc also responds to an anterior load by shifting posteriorly, the response of the device essentially mimics that of a natural intervertebral disc.

The materials for the core and endplates are biocompatible and generally similar to those disclosed in the prior art. Examples of such material pairs are metal on polyethylene, metal on metal, and ceramic on ceramic.

In preferred embodiments, each of the inferior endplate, superior endplate, core member and shock-absorbing component is manufactured from a material that possesses the strength and high wear resistance desired for use as a motion disc component.

These components of the present invention may be made from any non-resorbable material appropriate for human surgical implantation, including but not limited to, surgically appropriate metals, and non-metallic materials, such as carbon fiber composites, polymers and ceramics.

In some embodiments, the core material is selected from the group consisting of polyethylene, PEEK, ceramic and metallic. The shock-absorbing component is preferably a biocompatible material without carbon black. The prosthetic endplate material is preferably selected from the group consisting of metal and composite (such as PEEK/carbon fiber).

If a metal is chosen as the material of construction for a component, then the metal is preferably selected from the group consisting of nitinol, titanium, titanium alloys (such as Ti-6Al-4V), chrome alloys (such as CrCo or Cr—Co—Mo) and stainless steel.

If a polymer is chosen as a material of construction for a component, then the polymer is preferably selected from the group consisting of polyesters, (particularly aromatic esters such as polyalkylene terephthalates, polyamides; polyalkenes; poly(vinyl fluoride); PTFE; polyarylethyl ketone PAEK; and mixtures thereof.

If a ceramic is chosen as the material of construction for a component, then the ceramic is preferably selected from the group consisting of alumina, zirconia and mixtures thereof. It is preferred to select an alumina-zirconia ceramic, such as BIOLOX Delta™, available from CeramTec of Plochingen, Germany. Depending on the material chosen, a smooth surface coating may be provided thereon to improve performance and reduce particulate wear debris.

In some embodiments, the core member is polyethylene. In others, it is a ceramic.

In some embodiments, the first endplate consists essentially of a metallic material, preferably a titanium alloy or a chrome-cobalt alloy. In some embodiments, the second endplate consists essentially of the same metallic material as the first plate. In some embodiments, the articulation surfaces of the endplates may be coated with a wear-resistant coating, such as diamond film, in order to reduce wear.

In some embodiments, the endplates are made of a stainless steel alloy, preferably BioDur$^R$ CCM Plus$^R$ Alloy available from Carpenter Specialty Alloys, Carpenter Technology Corporation of Wyomissing, Pa.; and the core member is made of polyethylene, preferably Marathon™, available from DePuy Orthopaedics of Warsaw, Ind. In some embodiments, the endplate endsurfaces are coated with a sintered beadcoating, preferably Porocoat™, available from DePuy Orthopaedics of Warsaw, Ind.

In some embodiments, the endplates are made from a composite comprising carbon fiber. Composites comprising carbon fiber are advantageous in that they typically have a strength and stiffness that is superior to neat polymer materials such as a polyarylethyl ketone PAEK. In some embodiments, each endplate is made from a polymer composite such as a PEKK-carbon fiber composite.

Preferably, the composite comprising carbon fiber further comprises a polymer. Preferably, the polymer is a polyarylethyl ketone (PAEK). More preferably, the PAEK is selected from the group consisting of polyetherether ketone (PEEK), polyether ketone ketone (PEKK) and polyether ketone (PEK). In preferred embodiments, the PAEK is PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present in a chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite comprises:
a) 40-99% (more preferably, 60-80 vol %) polyarylethyl ketone (PAEK), and
b) 1-60% (more preferably, 20-40 vol %) carbon fiber,
wherein the polyarylethyl ketone (PAEK) is selected from the group consisting of polyetherether ketone (PEEK), polyether ketone ketone (PEKK) and polyether ketone (PEK).

In some embodiments, the composite consists essentially of PAEK and carbon fiber. More preferably, the composite comprises 60-80 wt % PAEK and 20-40 wt % carbon fiber. Still more preferably the composite comprises 65-75 wt % PAEK and 25-35 wt % carbon fiber.

Generally, the peripheral shock-absorber is made of nitinol or an elastomer, and is preferably an elastomer as selected in U.S. Pat. No. 5,824,094 ("Serhan"), the specification of which is incorporated by reference in its entirety. In some embodiments, the elastomeric shock-absorber is preferably made of a polyolefin rubber or carbon black reinforced polyolefin rubber. The hardness of the elastomeric shock-absorber is preferably 56-72 shore A durometer. The ultimate tensile strength of the shock-absorber is preferably greater than 1600 psi. The shock-absorber preferably has an ultimate elongation greater than 300% using the ASTM D412-87 testing method, and a tear resistance greater than 100 psi using the ASTM D624-86 testing method. Although the elastomeric shock-absorber is disclosed as being made of a polyolefin rubber, it can be made of any elastomeric material that simulates the characteristics of a natural disc.

Although the present invention has been described with reference to its preferred embodiments, those skillful in the art will recognize changes that may be made in form and structure which do not depart from the spirit of the invention.

We claim:

1. A motion disc comprising:
   a) a first prosthetic vertebral endplate comprising:
      i) a first outer surface adapted to mate with a first vertebral body,
      ii) a first inner surface comprising an first peripheral surface and a first articulation surface,
      iii) a body portion connecting the first inner and outer surfaces,
   b) a second prosthetic vertebral endplate comprising:
      i) a second outer surface adapted to mate with a second vertebral body, and
      ii) a second inner surface comprising a second peripheral surface and a second articulation surface,
      iii) a body portion connecting the second inner and outer surfaces,
   c) an articulating core member comprising:
      i) a first articulation surface adapted for articulation with the first articulation surface of the first endplate, and
      ii) a second articulation surface adapted for articulation with the first articulation surface of the second endplate,
   d) a peripheral, helical shock-absorbing component comprising:
      i) a first end portion contacting the first endplate, and
      ii) a second end portion contacting the second endplate, and
      iii) an axial channel,
   wherein the core member is disposed within the axial channel of the helical shock-absorbing component and oriented therein to produce a first articulation interface between the first articulation surface of the first endplate and the first articulation surface of the core member, and a second articulation interface between the first articulation surface of the second endplate and the second articulation surface of the core member,
   further comprising a sheath adapted to at least partially enclose the articulation surfaces, wherein the sheath is located between the core and the peripheral, helical shock-absorbing component.

* * * * *